(12) United States Patent
Depalo et al.

(10) Patent No.: US 11,052,003 B2
(45) Date of Patent: Jul. 6, 2021

(54) WHEELCHAIR WITH INTEGRATED TRANSFER DEVICE

(71) Applicant: RIGOLIO EMILIO, Busto Arsizio (IT)

(72) Inventors: Andrea Depalo, Saronno (IT); Emilio Rigolio, Busto Arsizio (IT); Antonino Quartarone, Paderno Dugnano (IT); Giovanni Cermola, Milan (IT)

(73) Assignee: AVANCHAIR S.R.L., Caronno Pertusella (IT)

( * ) Notice: Subject to any disclaimer, the term of this patent is extended or adjusted under 35 U.S.C. 154(b) by 252 days.

(21) Appl. No.: 16/204,241

(22) Filed: Nov. 29, 2018

(65) Prior Publication Data

US 2019/0167497 A1    Jun. 6, 2019

(30) Foreign Application Priority Data

Dec. 5, 2017  (IT) .................. 102017000139870

(51) Int. Cl.
| | |
|---|---|
| *A61G 5/10* | (2006.01) |
| *A61G 7/10* | (2006.01) |
| *A61G 5/12* | (2006.01) |
| *A61B 5/00* | (2006.01) |
| *B60B 19/00* | (2006.01) |
| *A61G 5/04* | (2013.01) |

(52) U.S. Cl.
CPC .......... *A61G 5/1056* (2013.01); *A61B 5/0002* (2013.01); *A61B 5/6894* (2013.01); *A61G 5/04* (2013.01); *A61G 5/10* (2013.01); *A61G 5/1059* (2013.01); *A61G 5/1062* (2013.01); *A61G 5/122* (2016.11); *A61G 5/125* (2016.11); *A61G 7/103* (2013.01); *A61G 7/1025* (2013.01); *A61G 7/1034* (2013.01); *B60B 19/003* (2013.01); *A61G 7/1065* (2013.01)

(58) Field of Classification Search
CPC ..... A61G 5/1056; A61G 7/051; A61G 7/0516
See application file for complete search history.

(56) References Cited

U.S. PATENT DOCUMENTS

| | | | | |
|---|---|---|---|---|
| 4,155,588 A | * | 5/1979 | Danziger ................. | A61G 5/00 297/115 |
| 5,060,960 A | * | 10/1991 | Branscumb ............ | A61G 7/103 280/250.1 |

(Continued)

*Primary Examiner* — Ruth Ilan
*Assistant Examiner* — Myles A Harris
(74) *Attorney, Agent, or Firm* — Cantor Colburn LLP (57) ABSTRACT

A wheelchair including a supporting frame and moving means configured to allow the movement of the wheelchair, the supporting frame having a seating area for a user of the wheelchair, the wheelchair including first actuation means configured to translate the seating area laterally and externally with respect to the supporting frame and, at least partially, with respect to the moving means, in a transfer configuration of the user, supporting means being operationally associated with the seating area, being able to be activated in the transfer configuration of the seating area to support the seating area with respect to the ground, the seating area being defined, in the transfer configuration, by a main seat and a secondary seat able to be activated in the transfer configuration of the seating area to increase the extension of the main seat.

11 Claims, 4 Drawing Sheets

(56) References Cited

U.S. PATENT DOCUMENTS

| | | | | |
|---|---|---|---|---|
| 5,193,633 | A * | 3/1993 | Ezenwa | A61G 5/006 180/271 |
| 5,517,704 | A | 5/1996 | Dagostino | |
| 6,325,399 | B1 * | 12/2001 | DeMoss | A61G 5/1059 280/250.1 |
| 6,361,267 | B1 * | 3/2002 | Chuang | A61G 5/00 280/304.1 |
| 6,802,518 | B2 * | 10/2004 | Kuntz | A61G 5/10 280/149.2 |
| 8,662,515 | B2 * | 3/2014 | Tsai | A61G 7/1036 280/250.1 |
| 8,684,398 | B1 * | 4/2014 | Nyitray | A61G 5/1075 280/657 |
| 9,662,255 | B2 * | 5/2017 | Wechter | A61G 7/1003 |
| 9,717,636 | B1 * | 8/2017 | Blanco | A61G 5/04 |
| 10,391,007 | B2 * | 8/2019 | Bryant | A61G 5/1059 |
| 10,434,023 | B1 * | 10/2019 | Fonarow | A61G 7/1026 |
| 2010/0154116 | A1 * | 6/2010 | Fan | A61G 7/1019 5/86.1 |
| 2012/0292883 | A1 * | 11/2012 | Noonan | A61G 5/006 280/304.1 |
| 2012/0295778 | A1 * | 11/2012 | Johansson | A63B 23/03525 482/131 |
| 2016/0101664 | A1 * | 4/2016 | Richter | A61G 5/1059 701/49 |
| 2016/0143794 | A1 * | 5/2016 | Balderson | A61G 5/125 280/250.1 |
| 2018/0014988 | A1 * | 1/2018 | Diaz-Flores | A61G 5/04 |
| 2018/0271334 | A1 * | 9/2018 | Hart | A47K 11/06 |
| 2020/0163819 | A1 * | 5/2020 | Cheek | A61G 7/1017 |

* cited by examiner

WHEELCHAIR WITH INTEGRATED TRANSFER DEVICE

CROSS REFERENCE TO RELATED APPLICATION

This application is related to and claims the benefit of Italian Patent Application Number 102017000139870 filed on Dec. 5, 2017, the contents of which are herein incorporated by reference in their entirety.

TECHNICAL FIELD

The present disclosure relates to a wheelchair with integrated transfer device.

BACKGROUND

It is known that people with disabilities who use walking aids need to move from the aid itself in the ordinary activities of daily life, moving themselves to other surfaces, for example a bed, a toilet, the seat of a car or a sofa.

There are currently several devices for assisted transfer on the market.

There are more basic devices, such as boards and cushions that facilitate the rotation of the user's body, and more complex systems, of the electromechanical type.

The (so-called) "transfer board" is a board adapted to transfer the user from a bed to a wheelchair, and vice versa, or from a wheelchair to a seat of a car, and vice versa. It can also be used for the transfer from a wheelchair to a toilet.

This tool has the following disadvantages:

It is usually placed on the lateral end of the wheelchair and on the lateral end of the surface to be reached. As it is in no way fixed, it can still move or slip, compromising the transfer.

In the presence of a manual wheelchair, the board must still be placed over the wheel, in this way the board will no longer be completely level, making the transfer uncomfortable.

As the board is not integrated into the wheelchair, it must necessarily "move with the user" and can therefore be forgotten during the transfers.

Other known transfer systems consist of cushions equipped with a non-slip lower surface and an upper surface rotatably associated with the lower surface, which makes it easier for the user to rotate to get in or out of a car and can also be used by rear seat passengers. However, they do not make it possible to compensate for the lateral distance between the seat of the car and that of the wheelchair.

To avoid this, it is possible to install special electric flaps on the vehicle which are designed to create a connecting bridge between the seat of the car and the wheelchair; however, this system obliges the owner to make a rather expensive modification to the vehicle and requires the consequent new approval of the vehicle itself.

There is also a system that envisages the use of a sliding seat, which can be integrated into a wheelchair or used as an accessory for a wheelchair. This system aims to help the user in the operations of getting into and out of a motor vehicle, and consists of a rack, a connecting cushion and an extender. However, this system forces the user to require the assistance of another person. This limits the possibilities of use, effectively excluding disabled people with driving licenses who need help to get into the driver's seat more comfortably. Furthermore, once the transfer system has fulfilled its function, there is still the remaining problem of how to load it in the boot of the car, together with the frame of the wheelchair to which it was attached. This operation must necessarily be performed by another person.

Finally, its scope of use is confined only to the car.

Such systems of known type are often subject to considerable overturning risks.

To overcome this, some wheelchairs have been patented which incorporate a transfer system, of which we find some examples in the prior art:

The first example is the following: a wheelchair which integrates a transfer device, which includes a base frame, an elevation unit and a transfer unit. In this way, a caregiver can easily and quickly move the disabled person from the wheelchair to another surface.

This transfer device is composed of a secondary seating surface, placed under the main seat, which is laterally extracted and placed on the surface to be reached, for example a bed, a toilet or a seat of a car. However, this transfer device suffers from the drawback of not guaranteeing a stable transfer plane between the main seat of the wheelchair and the surface to be reached, since the distance between the wheelchair and the surface to be reached or the height of the surface to be reached can vary significantly, with possible and unpredictable negative consequences on the stability of the transfer plane.

A second known device consists of an electric wheelchair, whose seat frame is arranged on a main frame, so as to be translated laterally until it is positioned above the traction wheels. Furthermore, in order to adjust the height of the seat, this device is equipped with a lifting device. In this device it is possible to perform the lateral translation of the seat even after the height has been adjusted. However, even this device belonging to the state of the art suffers from drawbacks related to the stability of the device itself. For example, in relation to the weight of the user and the physical movements that he or she makes during the transfer, the electric wheelchair could even overturn.

Therefore, three limits can be highlighted:

1) The excursion of the seat is limited to covering the gap created by the driving wheels alone. This makes it more difficult to reach surfaces that, for reasons of space, are positioned at a certain distance from the driving wheels.

2) The lack of a secondary seat, or of an extended portion of the seating surface, connects the possibility of lateral excursion to the width of the user's seat (which establishes the maximum size of the seating surface), even if it is possible to translate the seat slightly outside the driving wheels, by virtue of their relative barycentre. It should be noted that the width of the seats varies for an adult subject from about 380 mm to about 640 mm and that a larger seating surface makes it possible to cover a wider gap during the lateral translation of the seat.

3) The lack of a supporting element makes it unsafe to translate the seat beyond the limit of the driving wheels.

Moreover, in the systems of the type described above it is generally not possible to adjust the seat height after the lateral translation thereof.

BRIEF SUMMARY

The aim of the present disclosure is to provide a wheelchair which solves the problems described above, obviating the drawbacks and overcoming the limits of the prior art, allowing the user to transfer to any surface in an autonomous and physically inexpensive way, without having to depend on the help of others.

The allows the user to operate the transfer from one surface to another with stability and security.

The disclosure further allows the user to be able to travel on any type of surface and to overcome the obstacles commonly found in the roadway (holes, sidewalks, curbs, etc.).

More particularly, the disclosure provides a wheelchair 1 comprising a supporting frame 2 and moving means 3 configured to allow the movement of said wheelchair 1, said supporting frame 2 comprising a seating area 4 for a user of said wheelchair 1, said wheelchair 1 comprising first actuation means 5 configured to let said seating area 4 translate laterally and externally with respect to said supporting frame 2 and, at least partially, with respect to said moving means 3, in a transfer configuration of said user, supporting means 6 being operationally associated to said seating area, being able to be activated in said transfer configuration of said seating area 4 to support said seating area 4 with respect to the ground, said seating area 4 being defined, in said transfer configuration, by a main seat 7 and a secondary seat 8 able to be activated in said transfer configuration of said seating area 4 to increase the extension of said main seat 7.

BRIEF DESCRIPTION OF THE DRAWINGS

Additional features and advantages will become more apparent from the description of four preferred, but non-exclusive, embodiments of a mobile device, particularly for disabled people, illustrated by way of non-limiting example with the aid of the appended drawings, in which.

DETAILED DESCRIPTION

Figure 1:
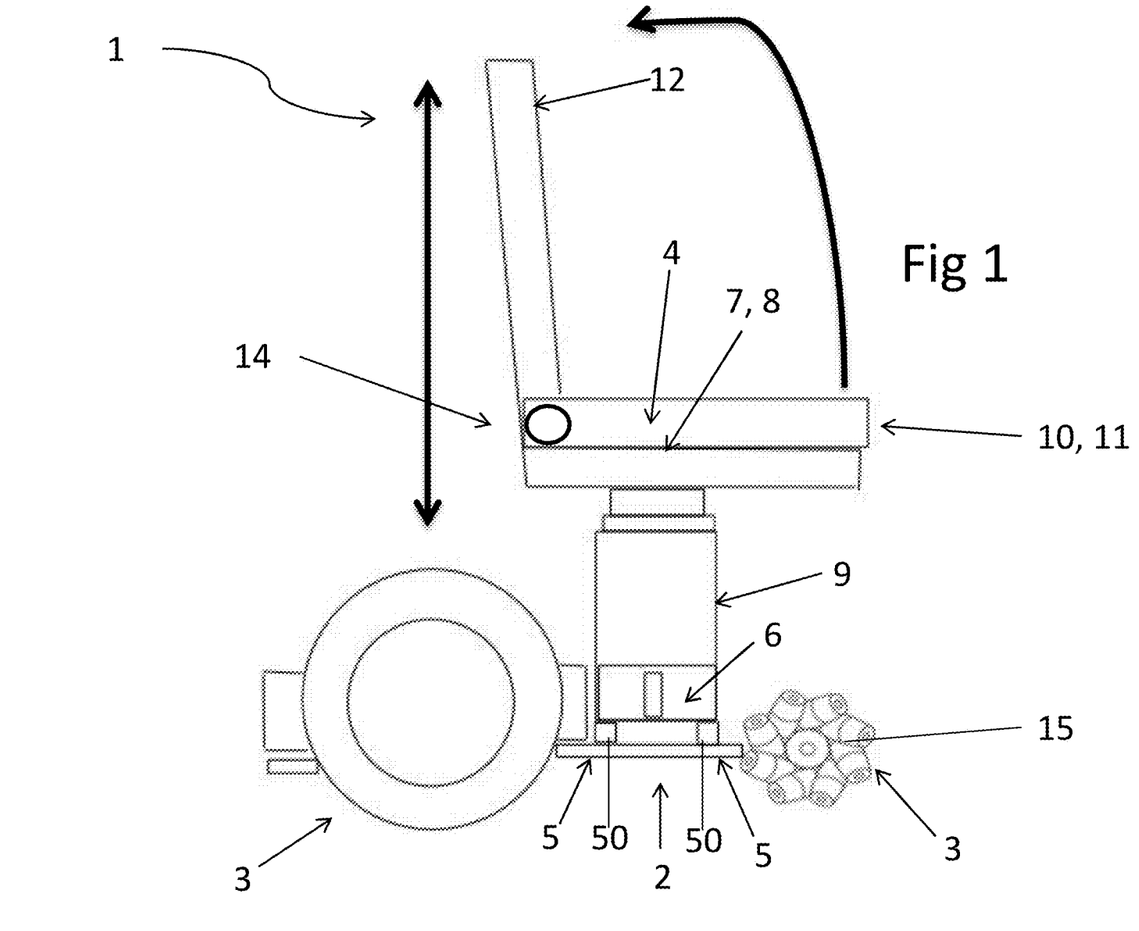
FIG. 1 is a side view of one of the possible embodiments of a wheelchair according to the disclosure.
Figure 2:
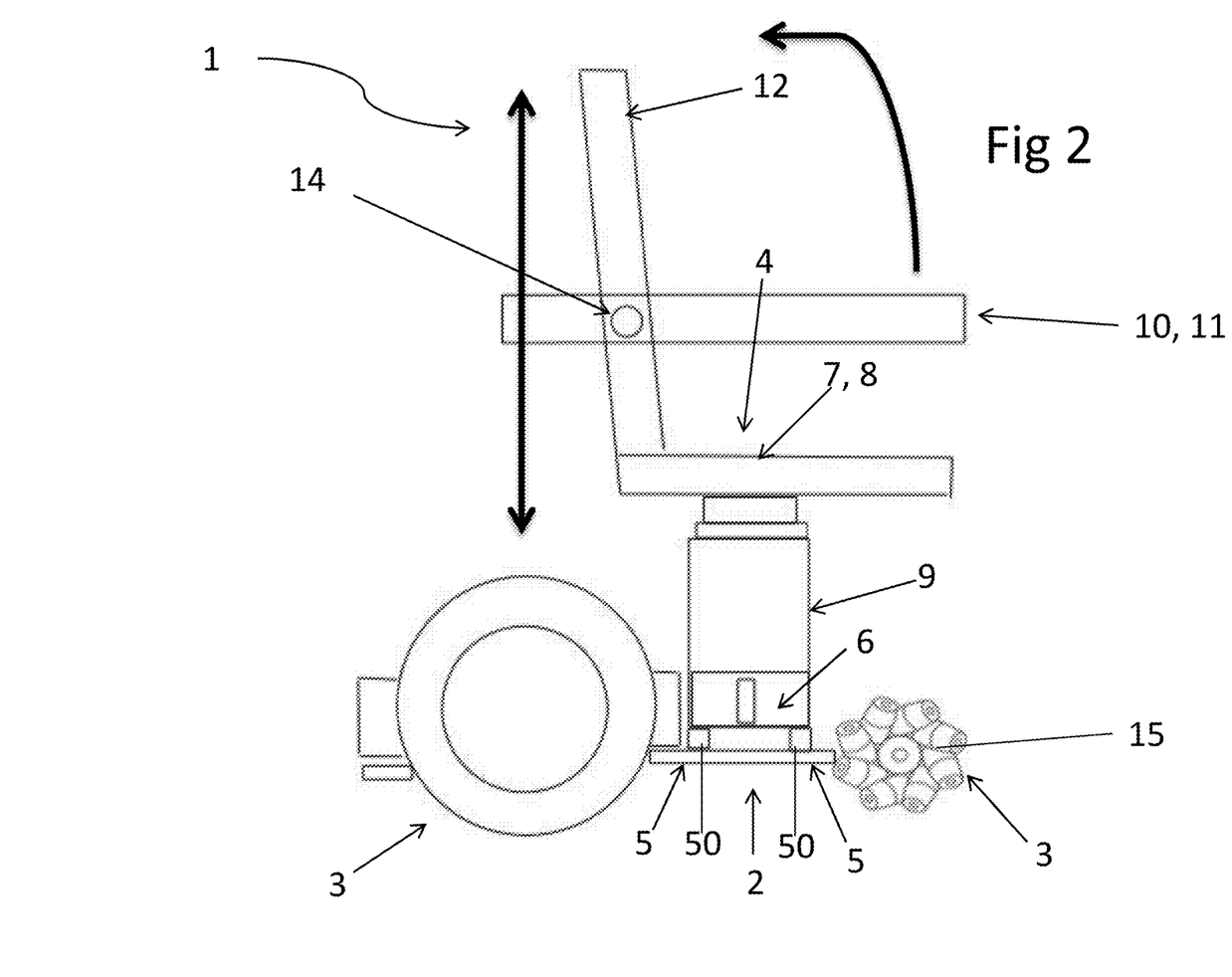
FIG. 2 is a further side view of one of the possible embodiments of a wheelchair according to the disclosure, in a different operating configuration.
Figure 3:
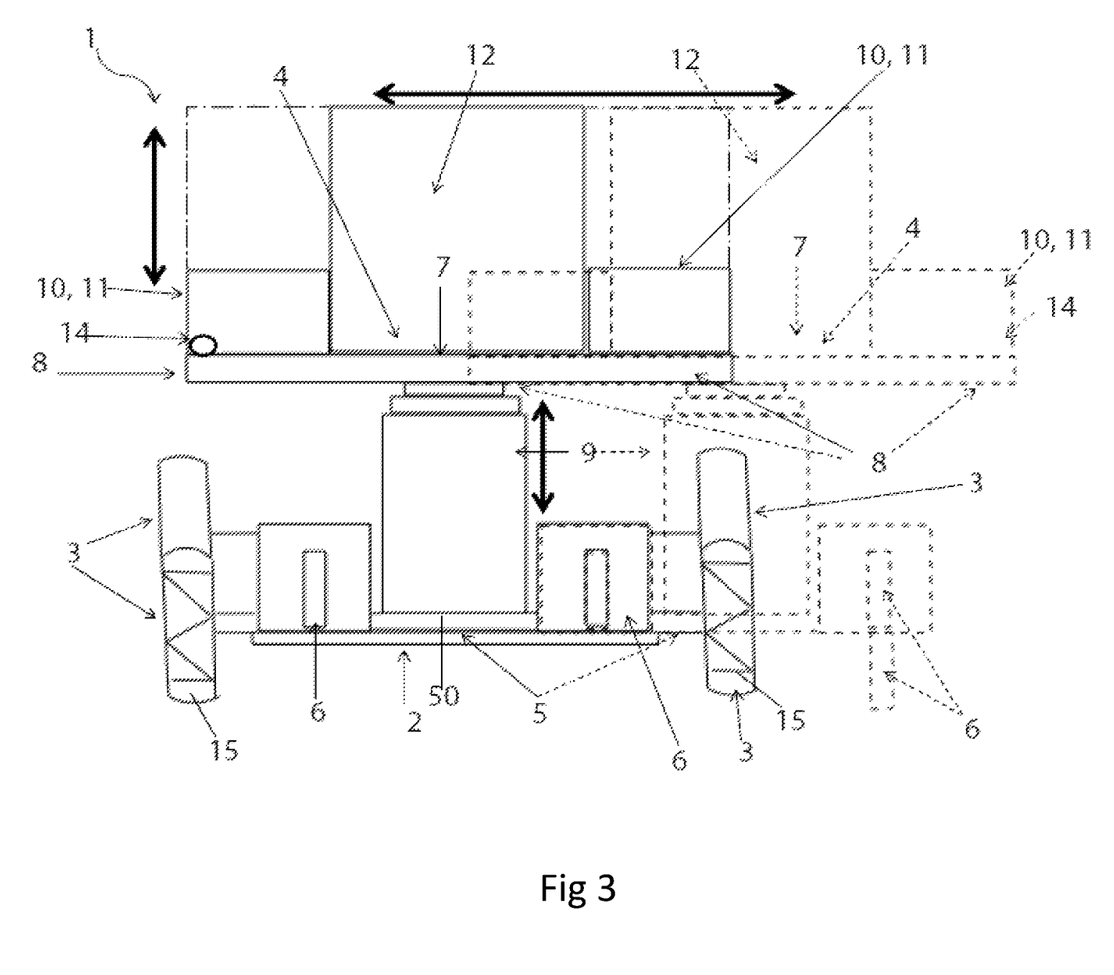
FIG. 3 is a front view of the wheelchair of FIGS. 1 and 2, according to the disclosure.

With reference to the aforementioned figures, the wheelchair, generally indicated by the reference number 1, comprises a supporting frame 2, to which moving means 3 are connected, configured to allow the movement of said wheelchair 1.

The supporting frame 2 comprises a seating area 4 for a wheelchair user.

The wheelchair 1 comprises first actuation means 5 (hereinafter also called horizontal translation means 5) configured to translate said seating area 4 laterally and externally with respect to the supporting frame 2 and, at least partially, with respect to the moving means 3, in a configuration of transfer of said user. Supporting elements 6 are operationally associated to said seating area 4, wherein said supporting elements 6 are able to be activated in said transfer configuration of said seating area 4 to support said seating area 4 with respect to the ground. In the transfer configuration said seating area 4 is defined, by a main seat 7 and by a secondary seat 8 able to be activated in said transfer configuration of said seating area 4 to increase the extension of said main seat 7.

Advantageously, the wheelchair 1 comprises second actuation means 9 (hereinafter also called vertical translation means 9) configured to raise up and lower down vertically said seating area 4, even when said seating area 4 is translated externally with respect to said supporting frame 2.

Said moving means 3 can advantageously be two pairs of wheels: the first pair, advantageously in the rear, is a traction (or power) pair of wheels, while the second is constituted by free wheels.

The pair of free wheels is advantageously constituted by omnidirectional type, non-pivoting wheels 15 (or "omniwheel" or "Swedish wheel" or "mecanum"), given their ability to move in an omnidirectional manner, which facilitates the approach to the surface to which the seat must be translated, in addition to reducing the turning radius of the wheelchair, compared to tilting wheels.

Said pair of free wheels can also have, in an alternative embodiment, an axis of shorter length with respect to that of the traction wheels (in said embodiment the distance between the wheels forming the front pair will be less than the distance between the wheels forming the rear pair), to facilitate the approach to surfaces such as the seat of a car.

The supporting frame 2 also houses the suitable vertical 9 and horizontal 5 translating means, adapted to house and to move in the disclosure, a seat 4 where the user sits. Advantageously, said vertical 9 and horizontal 5 translating means are able to translate said seat 4 laterally and externally with respect to said supporting frame 2 and, at least partially, with respect to the moving means 3, in a transfer configuration.

The vertical translating means 9 constitute said second actuation means configured for vertically raising and lowering said seat 4, preferably also externally to the supporting frame 2.

The vertical translating means 9, which support the seat 4, are in fact connected to the horizontal translating means 5. In this way both the seat 4 and the vertical translating means 9 can be moved, by means of the horizontal translating means 5, externally to the supporting frame 2, allowing the adjustment of the height of the seat 4 from the ground, even when the latter is translated externally to the supporting frame 2.

Advantageously, therefore, this horizontal translating means 5, hereinafter also called horizontal translating mechanism 5, can be constituted by telescopic rails 50 which allow the lateral displacement (right and left) of the entire seat assembly.

Said seat assembly consists of the vertical translating means 9 (advantageously of the telescopic column type, or of the pantograph hoist type), the lateral supporting elements 6 and the seat 4 itself, complete with accessories.

Advantageously, the mechanism which allows movement to the right and left can contain a rack (or, in an alternative embodiment, also two racks) fixed to the telescopic rails, which is actuated by a pinion (which in the case of using two racks, moves in the direction of displacement) placed on a gear motor, causing the displacement to occur.

The seat 4 which can be moved externally to the supporting frame 2 is advantageously composed of a main seat 7, and relative accessories, such as for example armrests 11 and a backrest 12.

The particular feature of said main seat 7 is that it is also provided with an extended portion of the seating surface, which is also adapted to be translated together with the seat 4 itself. Said extended portion of the seating surface is that portion of the seating surface exceeding the main seat 7, able to be activated in the transfer configuration of the seat 4 to increase the extension of the main seat.

The purpose of said extended portion of the seating surface, in fact, is that of bridging the possible gap created as a result of the use of the horizontal translating means 5 (as a result of their extending externally to the supporting frame) and of facilitating the user in his or her movements, making it possible to bring the user closer to the surface to be reached, ensuring a smooth and continuous surface with which to carry out the transfer.

Advantageously, the extended portion of the seating surface can consist of two secondary seats 8, one on each side, placed side by side with the main seat 7. Said secondary seat 8 can be provided with a backrest adapted to close on the secondary seat 8, thanks to suitable actuation means 14. In this way said secondary seats 8 act as an armrest 11 for the main seat 7.

During the transfer, the armrest/backrest 11 of the secondary seat 8, located on the side involved in the transfer, from the position wherein it is normally closed on the secondary seat (horizontal) 8, thanks to suitable actuation means 14, is brought into a vertical (or semi-vertical) position. In this way said secondary seat 8 stops acting as an armrest 11 for the main seat 7, extending the backrest 12 and making the extended portion of the seating surface usable for the user.

In a variant of the same embodiment, the extended portion of the seating surface can consist of a single seating surface, also comprising the extended portion. The seating surface can be equipped with a backrest, divided into three parts. The two lateral portions of the backrest are adapted to close, also individually, on the extended portions of the seating surface 4, thanks to suitable actuation means 14. In this way, these lateral portions of the backrest act as an armrest 11 for the main seat 7 and delimit the extended portion of the seating surface.

In both variants of this first embodiment, it is therefore clear that the armrests 11 can be lifted, also individually, in alignment with the backrest of the main seat 7, and the secondary seat 8 (defined respectively on the sides of the main seat) consists of a portion of the main seat extending horizontally at said armrests. In the second variant of this first embodiment, the secondary seat 8 and the main seat 7 are part of a single seating plane, while in the first variant the secondary seat 8 and the main seat 7, separated, constitute a shared seating plane.

In one possible alternative embodiment, the seat can advantageously be provided with a couple of lateral containment supports 10, adapted to contain the user's seat and movable by suitable actuation means, so as to be carried, also individually, in a position which does not obstruct the transfer. Advantageously, lateral containment supports 10 of the "lateral trunk thrusts" type can be used with a swing-away type mechanism or, alternatively and advantageously, another means suitable for carrying out a lateral containment of the seat and/or of the trunk, which can be externally or posteriorly overturned to the seat surface. The task of said feature is that of defining the portion of the seating surface included between the two so-called "lateral trunk thrusts" (or the two means suitable for carrying out a lateral containment of the seat and/or trunk) as part of the main seat 7, thus defining the remaining part of the seating surface as an extended portion of the seating surface.

In this case, the secondary seat 8 is defined by the extended seat, having a single seating surface and the lateral supports are brought into an overturned position in the rear or externally to the seating surface, when the seat itself is in the transfer configuration, allowing the user to translate freely.

It should be noted that both the extended portion of the seating surface and the possibility of adjusting the height of the seat itself constitute an advantage with respect to the known device provided with a removable seating surface, which envisages that the secondary seating surface is not placed at the same height as the main one, unless suitable means are provided for bringing it side by side, since this feature of the device of the known art can in fact create a further gap to be bridged during the transfer.

With respect to the known device constituted by an electric wheelchair, whose seating frame is arranged on a main frame so as to be laterally translated, the extended portion of the seating surface, together with the supporting lateral element, is an advantage, since it is possible to avoid connecting the possibility of lateral excursion to the width of the user's seat (which establishes the maximum size of the seating surface), also allowing the seat to be translated outside the driving wheels.

The disclosure is also provided with two lateral supporting elements 6 of the assembly relative to the seat 4, one on each side, adapted to avoid the overturning of the wheelchair 1 during the transfer operations. Said lateral supporting elements 6 can advantageously be constituted by a linear actuator provided, at the end, with a suitable element adapted to engage with the ground, advantageously a foot with anti-slip functions.

Said lateral supporting elements 6 are fixed to the structure of the lateral translation means 5 of the assembly relative to the seat 4. When the latter starts to translate externally to the supporting frame 2, bringing the middle of the seat 4 beyond the limit of the traction wheel 3, the lateral supporting elements 6 extend downwards thanks to suitable actuation means, touching ground.

In this way said supporting elements 6, able to be activated in said seat transfer configuration, will support the same with respect to the ground.

In one possible alternative embodiment, the lateral supporting elements 6 can advantageously be constituted by a linear actuator with a wheel (advantageously pivoting) at the end, adapted to engage with the ground.

Said lateral supporting elements 6 are always fixed to the structure of the lateral translation means. When the latter starts to translate externally to the supporting frame 2, bringing the middle of the seat 4 beyond the limit of the traction wheel 3, the lateral supporting elements 6 extend downwards thanks to suitable actuation means, touching the ground and allowing the wheel (advantageously pivoting) to engage with the ground.

Unlike the previous embodiment, the present embodiment allows the lateral supporting elements 6 to extend shortly after the stroke of the horizontal translating means 5 of the assembly relative to the seat 4 has begun, allowing the pivoting wheel to engage with the ground, and the lateral supporting elements 6 to accompany the lateral translation of the group relative to the seat 4.

This makes it possible to vary the positioning of the wheelchair 1 of the disclosure, with respect to the surface to be reached, even when the seat 4 is translated externally with respect to the supporting frame 2.

It should be noted that the known devices, which do not provide a supporting element, provided instead in the present disclosure, can imply the need to use the surface to be reached as a point of support. This operation can be accomplished if the surface is a bed, but it is difficult, if not impossible, if it is a smaller area such as a toilet or a seat of a car.

The wheelchair 1 further advantageously comprises a footrest, free on the sides and which can be closed by actuation means, inside the supporting frame 2.

Figure 4:
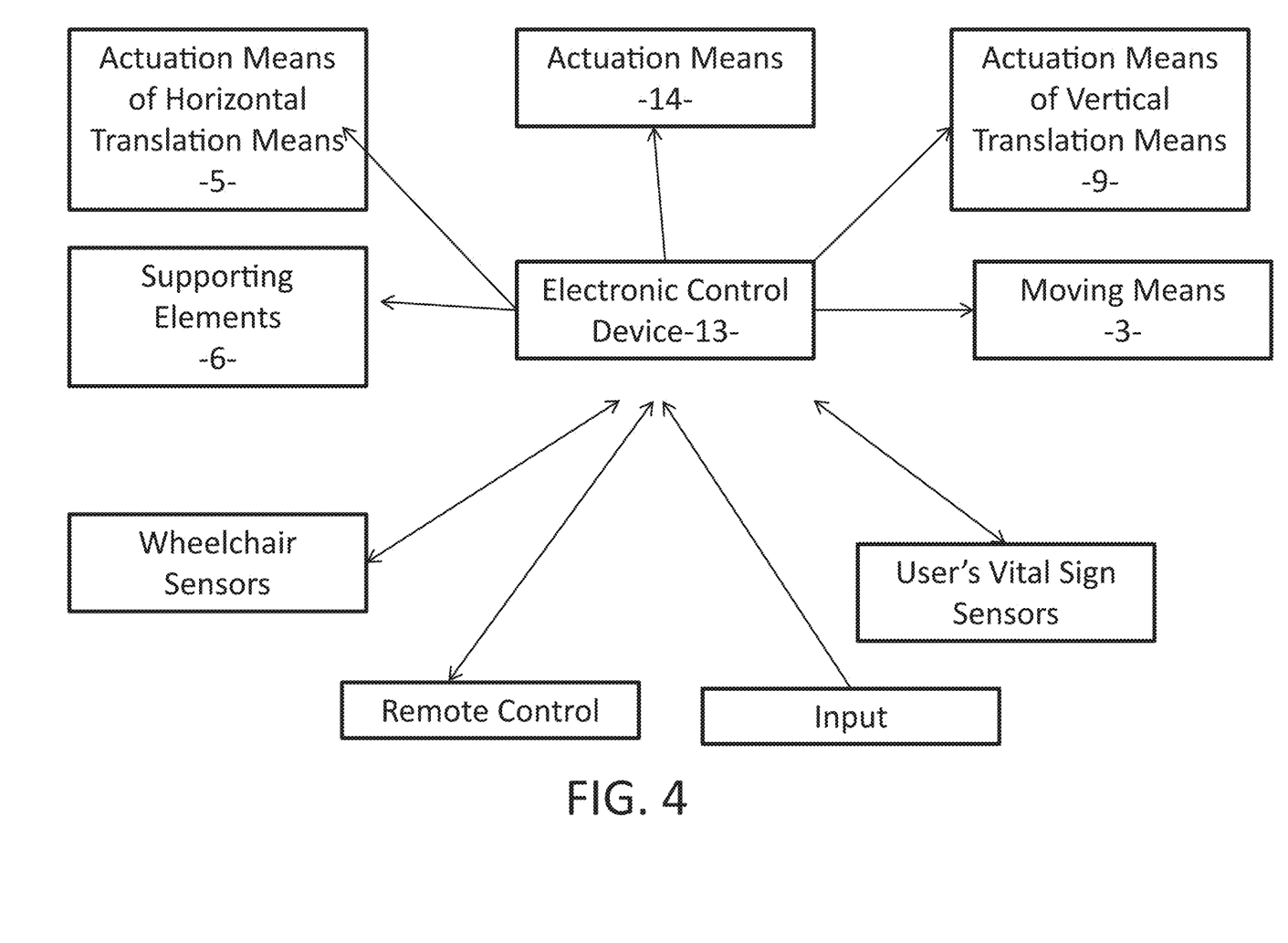
FIG. 4 is a logical diagram of the electronic control device comprised in the wheelchair of FIGS. 1, 2 and 3, according to the disclosure.

The wheelchair 1 further and advantageously comprises an electronic control device 13, advantageously computerized, adapted to monitor the user's vital signs, the wheelchair's operation parameters and the wheelchair's position, as well as adapted to control said moving means 3, the actuation means of the horizontal 5 and vertical 9 translation means, the actuation means 14 of the secondary seat 8 and said supporting elements 6.

Said control device 13 is also equipped with protocols adapted to monitor the user's vital signs, the wheelchair's operation parameters and the wheelchair's position, as well as to allow the remote control and use of the moving means 3 and/or of the actuation means of the horizontal 5 and vertical 9 translation means, and/or of the actuation means 14 of the secondary seat 8, and/or of the supporting elements 6.

Summarizing the operation of the disclosure in illustrative but not exhaustive terms, the transfer of the user from the seat to the surface to be reached, in the embodiment illustrated by the figures, can take place as follows:

1) From the seat 4, the user activates the necessary automations, activating the following operations: The user adjusts the height of the seat 4, through suitable actuation means of vertical translation means 9.
2) The seat assembly, with the user seated on it, translates externally with respect to the supporting frame 2 until reaching the surface on which to move or alternatively up to the maximum allowed lateral excursion.
2a) Only in the alternative embodiment wherein the lateral supporting elements 6 of the seat assembly engage the ground with a wheel (advantageously pivoting), the same extends shortly after the start, allowing the lateral supporting elements 6 to accompany the lateral translation of the seat assembly.
3) Only in the alternative embodiment wherein the lateral supporting elements 6 of the seat assembly are not provided with a wheel (advantageously pivoting): once the seat assembly has been translated laterally, the relative supporting elements 6 extend, engaging with the ground.
4) The user can intervene again to adjust the seat height, if necessary.
   b.1) The backrest of the secondary seat placed on the side involved in the transfer, normally closed on the secondary seat 8 is brought from the horizontal to the vertical position thanks to suitable actuation means 14. In this way said secondary seat 8 will stop functioning as an armrest 11 for the main seat 7, extending the main backrest 12 and making the extended portion of the seating surface usable to the user.
   b.2) In the alternative embodiment wherein the seat is provided with a couple of lateral containment supports 10, adapted to contain the user's seat (as opposed to the provisions of point b.1): The lateral containment supports 10, adapted to contain the user's seat are moved, thanks to suitable actuation means 14, in such a way as to be carried, also individually, into a position which does not hinder the transfer.
   c) The user can therefore freely move to the surface to be reached.

The wheelchair also advantageously comprises an electronic control device 13, advantageously composed of one or more MCUs (also called microcontrollers) adapted to control the user's vital signs, the wheelchair's operational parameters, the wheelchair's position, the moving means 3, the actuation means of horizontal 5 and vertical 9 translation means, the actuation means 14, and the supporting means 6. The control device, equipped with connectivity to internet, telephone and GSM networks, is preferably able, advantageously by using sensors such as:

- Accelerometer and Gyroscope
- Magnetometers
- Reed sensor
- Integrated pulse oximetry and heart-rate monitor sensor
- GPS (in an alternative embodiment, position tracking is performed using the cellular telephone network, advantageously GSM, and not GPS)

to send calls or emergency messages if the user falls or a sudden variation of his or her vital signs is detected, in addition to providing the wheelchair with an autonomous navigation capacity thanks to special sensors placed inside or on the surface of the disclosure (advantageously IR or Lidar).

The control device 13 will also provide information on the status of the batteries and any maintenance to be carried out, as well as allow the wheelchair 1 user the possibility to interrogate operating parameters, such as for example battery life, or to give voice commands and remote control, also through cloud-based services such as voice-controlled AI assistants.

The software infrastructure that supports the device will makes it possible to connect the wheelchair 1 to home automation and electric vehicle devices, as well as allow the user to hire the chair, with a pay-as-you go service, for example inside fairs, events or in public places.

The invention claimed is:

1. A wheelchair comprising;
   a supporting frame;
   moving means configured to move said wheelchair, said supporting frame comprising a seating area for a wheelchair user;
   first actuation means configured to translate said seating area laterally and externally with respect to said supporting frame and, at least partially, with respect to said moving means, in a configuration of transfer of said user;
   supporting elements being operationally associated to said seating area, said supporting elements being able to be activated in said transfer configuration of said seating area to support said seating area with respect to the ground,
   wherein said seating area being defined, in said transfer configuration, by a main seat and a secondary seat able to be activated in said transfer configuration of said seating area to increase the extension of said main seat.

2. The wheelchair, according to claim 1, further comprising second actuation means configured to raise up and lower down vertically said seating area, even when said seating area is translated externally with respect to said supporting frame.

3. The wheelchair, according to claim 1, wherein said main seat comprises a couple of lateral containment supports, suitable for containing the user's seat in said transfer configuration of said seating area, said couple of lateral containment supports being moved, even separately, in a position suitable for not hampering the user's transferring.

4. The wheelchair, according to claim 3, wherein said lateral containment supports suitable for containing the user's seat, are armrests.

5. The wheelchair, according to claim 4, wherein said armrests are movable upwards, even separately, in alignment with the backrest of said main seat, said secondary seat being defined respectively on either side of said main seat, by a portion of said main seat extending horizontally on either side of said main seat in a position corresponding to the position of said armrests.

6. The wheelchair, according to claim 5, wherein said secondary seat is defined respectively on either side of said main seat by a portion of said main seat extending horizontally on either side of said main seat in a position corresponding to the position of said armrests, said secondary seat and said main seat being part of a same seating plane.

7. The wheelchair, according to claim 1, further comprising an electronic control device suitable to monitoring user's vital signs, wheelchair's operation parameters and wheelchair's position, furthermore suitable to control said moving means, and/or said first actuation means and/or said second actuation means and/or actuation means of said secondary seat and/or said supporting elements.

8. The wheelchair, according to claim 1, further comprising an electronic control device including protocols to allow remote monitoring of user's vital signs, of wheelchair's operation parameters and wheelchair's position, furthermore including protocols to allow remote control of said moving means, and/or of said first actuation means, and/or of said second actuation means and/or of the actuation means of said secondary seat and/or of said supporting elements.

9. The wheelchair, according to claim 1, wherein said moving means are at least a couple of non-pivoting omni-directional wheels.

10. The wheelchair, according to claim 9, wherein the distance between the moving means forming a forward couple is shorter than the distance between the moving means forming a rear couple.

11. A wheelchair comprising:
a supporting frame;
moving means configured to move said wheelchair, said supporting frame comprising a seating area for a wheelchair user;
first actuation means configured to translate said seating area laterally and externally with respect to said supporting frame and, at least partially, with respect to said moving means, in a configuration of transfer of said user;
supporting elements being operationally associated to said seating area, said supporting elements being able to be activated in said transfer configuration of said seating area to support said seating area with respect to the ground,
wherein said seating area being defined, in said transfer configuration, by a main seat and a secondary seat able to be activated in said transfer configuration of said seating area to increase the extension of said main seat;
and wherein said main seat comprises a couple of armrests, suitable for containing the user's seat in said transfer configuration of said seating area, said couple of armrests being movable, even separately, in a position suitable for not hampering the user's transferring;
and in alignment with the backrest of said main seat, said secondary seat being defined respectively on either side of said main seat, by a portion of said main seat extending horizontally on either side of said main seat in a position corresponding to the position of said armrests.

* * * * *